United States Patent [19]

Pieper et al.

[11] Patent Number: 5,391,298
[45] Date of Patent: Feb. 21, 1995

[54] METHOD FOR PERFORMING A SOLID-PHASE EXTRACTION UNDER PRESSURIZED CONDITIONS

[75] Inventors: Richard M. Pieper, St. Paul; James E. Aysta, Stillwater, both of Minn.

[73] Assignee: Minnesota Mining and Manufacturing Company, St. Paul, Minn.

[21] Appl. No.: 27,080

[22] Filed: Mar. 5, 1993

[51] Int. Cl.6 .............................................. B01D 15/00
[52] U.S. Cl. ..................................... 210/638; 210/674; 210/679
[58] Field of Search ............... 210/674, 679, 691, 692, 210/638

[56] References Cited

U.S. PATENT DOCUMENTS

| | | | |
|---|---|---|---|
| 4,013,072 | 3/1977 | Jess | 128/214 C |
| 4,115,277 | 9/1978 | Swank | 210/436 |
| 4,172,790 | 10/1979 | Kubo | 210/137 |
| 4,294,594 | 10/1981 | Sloane, Jr. et al. | 55/186 |
| 4,348,280 | 9/1982 | George et al. | 210/101 |
| 4,411,783 | 10/1983 | Dickens et al. | 210/304 |
| 4,460,642 | 7/1984 | Errede et al. | 428/283 |
| 4,722,898 | 2/1988 | Errede et al. | 435/182 |
| 4,765,904 | 8/1988 | Kaplan | 210/637 |
| 4,789,468 | 12/1988 | Sirkar | 210/137 |
| 4,804,464 | 2/1989 | Schevey | 210/96.1 |
| 4,810,381 | 3/1989 | Hagen et al. | 210/502.1 |
| 4,871,671 | 10/1989 | Errede et al. | 435/182 |
| 4,944,876 | 7/1990 | Miller | 210/321.75 |
| 5,047,154 | 9/1991 | Comstock et al. | 210/636 |
| 5,071,565 | 12/1991 | Fritz et al. | 210/692 |
| 5,071,610 | 12/1991 | Hagen et al. | 264/120 |
| 5,113,860 | 5/1992 | McQuinn | 128/632 |
| 5,116,496 | 5/1992 | Scott | 210/232 |
| 5,124,041 | 6/1992 | Sheer et al. | 210/641 |
| 5,198,115 | 3/1993 | Stalling et al. | 210/137 |
| 5,205,989 | 4/1993 | Aysta | 422/101 |
| 5,238,621 | 8/1993 | Hagen et al. | 264/45.3 |
| 5,242,598 | 9/1993 | Shannon et al. | 210/909 |
| 5,248,428 | 9/1993 | Hagen et al. | 210/656 |
| 5,264,184 | 11/1993 | Aysta et al. | 422/101 |
| 5,279,742 | 1/1994 | Markell et al. | 210/638 |
| 5,328,758 | 7/1994 | Markell et al. | 428/281 |

FOREIGN PATENT DOCUMENTS

| | | | |
|---|---|---|---|
| 0213744A3 | 3/1987 | European Pat. Off. | B01D 13/04 |
| 0246065A1 | 11/1987 | European Pat. Off. | B01D 13/00 |
| WO93/00163 | 1/1993 | WIPO | B01J 20/28 |

OTHER PUBLICATIONS

D. Hagen et al., 236 Membrane Approach to Solid—Phase Extractions 157–164, 159 (1990).
Millipore Product Literature.

*Primary Examiner*—Ivars Cintins
*Attorney, Agent, or Firm*—Gary L. Griswold; Walter N. Kirn; Karl G. Hanson

[57] ABSTRACT

A method of performing a solid phase extraction on an aqueous fluid using a hydrophobic, solid-phase extraction medium (40), which method comprises:

(a) placing (10) a hydrophobic, solid-phase extraction medium (40) inside of a pressurizable housing (18) having an inlet (25) and an outlet (32), the hydrophobic, solid-phase extraction medium (40) being positioned in the pressurizable housing (18) such that a liquid moving from the inlet (25) to the outlet (32) passes through the solid-phase extraction medium (40);

(b) priming (12) the hydrophobic, solid-phase extraction medium (40) with a water-miscible organic liquid by passing the water-miscible organic liquid from the inlet (25) to the outlet (32) under positive pressure; and (c) passing (14) an aqueous liquid from the inlet (25) to the outlet (32) under positive pressure;

wherein the water-miscible organic liquid and aqueous liquid are passed from the inlet (25) to the outlet (32) such that the solid-phase extraction medium (40) is completely and continuously immersed in liquid in the pressurizable housing (18) during steps (b) and (c).

10 Claims, 2 Drawing Sheets

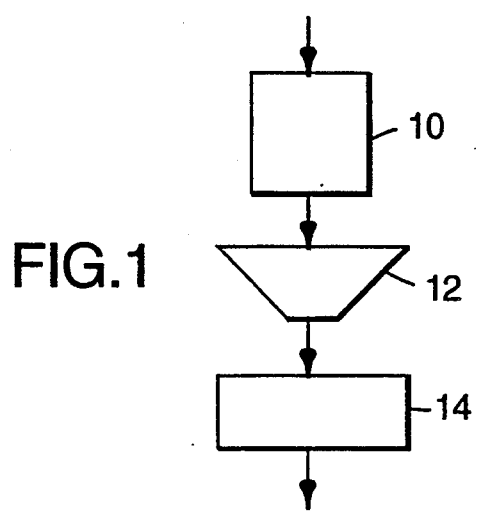
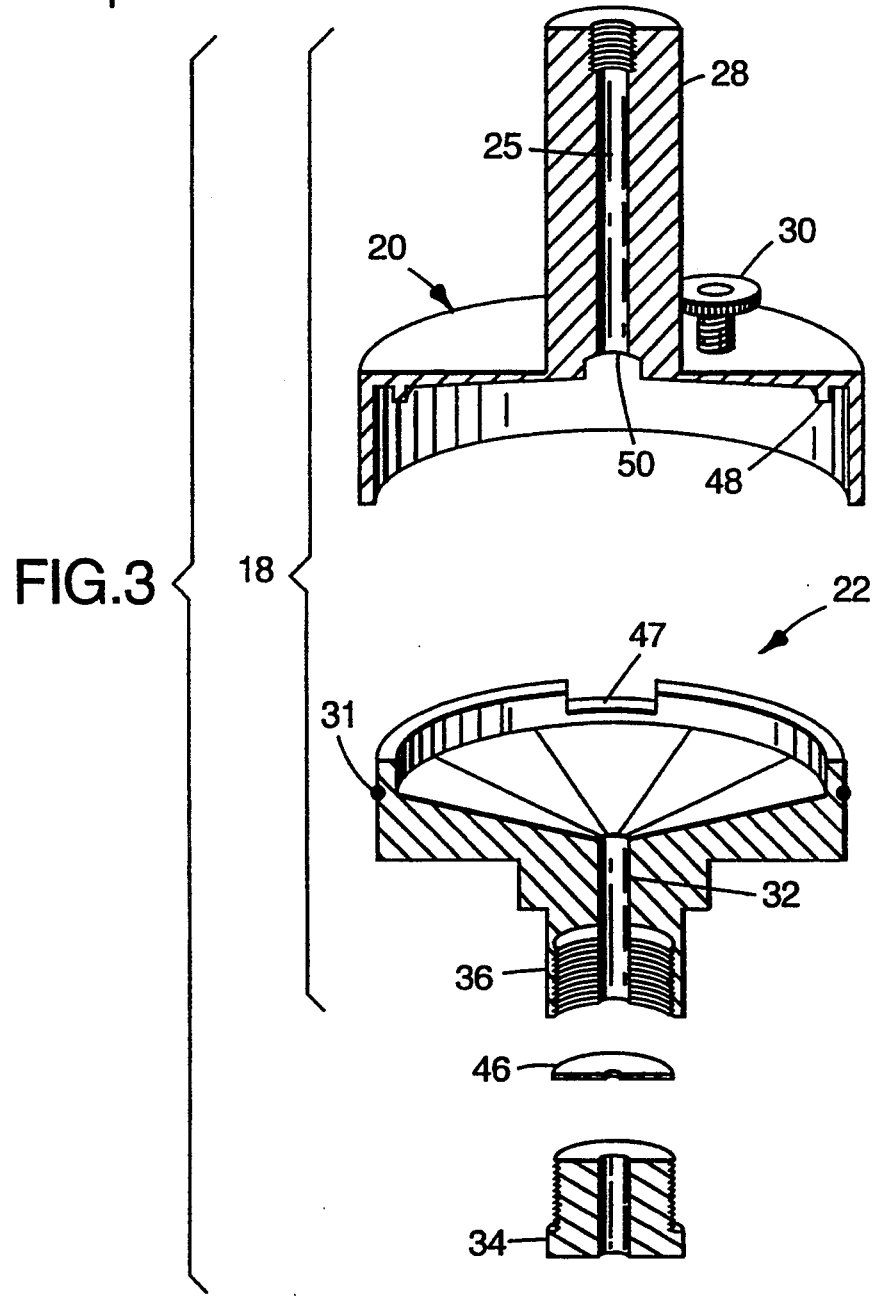

METHOD FOR PERFORMING A SOLID-PHASE EXTRACTION UNDER PRESSURIZED CONDITIONS

The present invention pertains to a method and apparatus for performing a solid-phase extraction through a hydrophobic, solid-phase extraction medium under pressurized conditions.

Solid-phase extraction (SPE) is a popular and growing technique for preparing samples for analysis. Sometimes referred to as liquid-solid extraction, SPE involves the use of a membrane or other medium that has sorptive properties. A fluid is passed through the SPE medium, and various materials in the fluid are extracted onto the SPE medium by being sorbed thereon or therein. The extracted molecular compounds can be removed from the SPE medium by desorbing the solids with an elution solvent to enable subsequent analysis of the compounds for composition, concentration, and the like. SPE is rapid, less labor-intensive than conventional liquid-liquid extractions, and it eliminates the need for large volumes of potentially hazardous or expensive solvents. Examples of the many applications for which SPE is used include determining trace amounts of pesticides in river water, analyzing for pollutants in waste water, isolating organic compounds from ground water, and pretreatment of urine samples.

While SPE has been met with increasing popularity in the analytical art, problems have been encountered in performing a SPE in a pressurized system using a hydrophobic SPE medium. When an aqueous liquid is passed through the hydrophobic SPE medium under a positive pressure, for example by use of a pump, the liquid frequently contains air bubbles which can come into contact with the SPE medium. When air contacts the hydrophobic SPE medium, the aqueous liquid no longer will wet that portion of the SPE medium. This minimizes or reduces the useful surface area of the SPE medium, and can increase processing time for a given volume of liquid, particularly when the processed liquid contains a high concentration of suspended solids. The reduction in useful surface area also can cause the SPE medium to lose capacity for extracted solubles. When loss of capacity occurs, solubles which would normally be sorbed by the SPE medium pass therethrough undetected. This undetected passage of solubles is referred to as "breakthrough", and it results in inaccurate analyses.

The present invention provides a method of performing SPE under pressurized conditions which prevents air from making contact with the SPE medium. The method therefore assures that essentially the whole surface area of the SPE medium is operative during the extraction so that processing time is minimized and breakthrough does not occur.

Briefly, the method of the invention comprises:
(a) placing a hydrophobic, solid-phase extraction medium inside of a pressurizable housing having an inlet and an outlet, the hydrophobic, solid-phase extraction medium being positioned in the pressurizable housing such that a liquid moving from the inlet to the outlet passes through the solid-phase extraction medium;
(b) priming the hydrophobic, solid-phase extraction medium with a water-miscible organic liquid by passing the water-miscible organic liquid from the inlet to the outlet under positive pressure; and
(c) passing an aqueous liquid from the inlet to the outlet under positive pressure;
wherein the water-miscible organic liquid and aqueous liquid are passed from the inlet to the outlet such that the solid-phase extraction medium is completely and continuously immersed in liquid in the pressurizable housing during steps (b) and (c).

The apparatus of the invention comprises:
(a) a pressurizable housing having an inlet and an outlet;
(b) a hydrophobic, solid-phase extraction medium disposed in the housing such that a liquid moving from the inlet to the outlet passes through the solid-phase extraction medium, the hydrophobic solid-phase extraction medium comprising a polytetrafluorethylene fibril matrix having sorptive particles enmeshed therein;
(c) a means for causing the liquid to pass from the inlet to the outlet under pressurized conditions; and
(d) a means for maintaining the hydrophobic, solid-phase extraction medium completely immersed in the liquid while the liquid is passing from the inlet to the outlet.

In the method and apparatus of this invention the hydrophobic SPE medium is kept completely and continuously immersed in liquid from the time of priming the hydrophobic medium until the aqueous liquid has been fully processed. Air is thereby precluded from making substantial contact with the SPE medium, and the whole surface of the SPE medium can be utilized during the SPE process. A liquid layer can be maintained over the SPE medium throughout fluid processing using one of the three different approaches, briefly described here.

In a first approach the pressurized or upstream side of the SPE medium is vented to the atmosphere until a liquid layer builds up over the surface of the hydrophobic SPE medium. After the liquid layer has a sufficient depth, the vent to the atmosphere is closed so that as additional liquid is pumped into the housing, pressure increases in the housing and forces the liquid to flow evenly through the hydrophobic SPE medium.

In a second approach the housing outlet has a restriction which reduces the liquid flow exiting the housing and thereby causes a liquid layer to build up in the housing which completely immerses the hydrophobic SPE medium. The restriction is fashioned to permit liquid to flow from the outlet only when enough liquid is present in the housing to completely cover the hydrophobic SPE medium.

In a third approach the SPE medium itself is used to restrict the fluid flow through the housing to allow a liquid layer to build up over the SPE medium. The housing is sized to provide room for a compressible air column over the SPE medium. When the liquid layer has sufficient depth to immerse the SPE medium, the air in the column above the SPE medium will exert sufficient pressure to overcome the resistance of the SPE medium, and the liquid will flow evenly therethrough.

In each of the described approaches, air does not come into contact with the SPE medium. Essentially the whole surface of the SPE medium can participate in the SPE process to enable quick, even flow of liquid through the SPE medium without breakthrough.

The above and other novel features and advantages of the invention are more fully described in the detailed description of the invention and drawings. It is to be expressly understood, however, that the description and drawings are for the purposes of illustrating the invention and are not to be read in a manner that would unduly limit the scope of the invention.

BRIEF DESCRIPTION OF THE DRAWINGS

FIG. 1 is a flow diagram generally illustrating the steps involved in the method of the present invention.

FIG. 3 is a sectional view of assembly 16 useful in the method of the present invention.

DETAILED DESCRIPTION OF THE PREFERRED EMBODIMENTS

Figure 2:
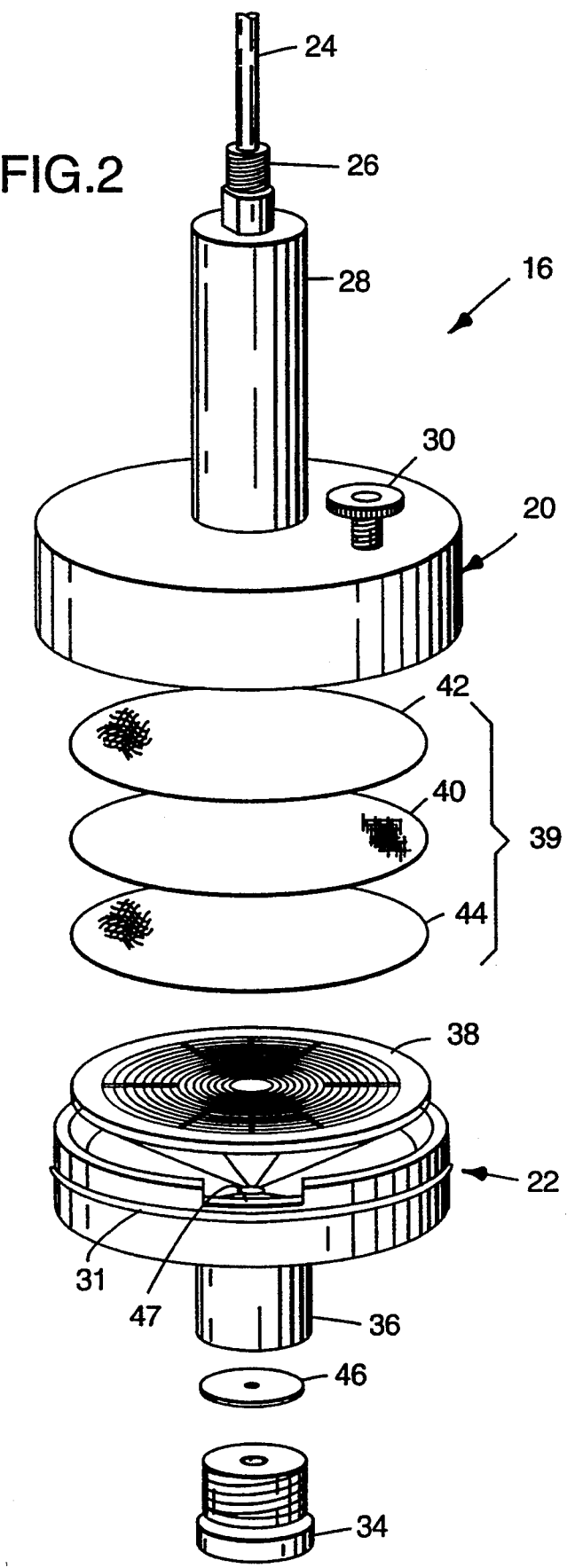
FIG. 2 is a perspective view of an assembly 16 useful in the method of the present invention.

In describing the preferred embodiments of the invention, specific terminology will be used for the sake of clarity. The invention, however, is not intended to be limited to the specific terms so selected, and it is to be understood that each term so selected includes all the technical equivalents that operate similarly.

FIG. 1 illustrates the sequence of steps that are employed in the present invention. In a first step 10, a hydrophobic SPE medium is placed in a pressurizable housing that has an inlet and an outlet. As used in here, the term "hydrophobic SPE medium" means a fluid-permeable mass that has sorptive properties and lacks an affinity for water. Generally speaking, a SPE medium is hydrophobic when it has a surface energy in the range of 20 to 300 millinewtons per meter (mN/M), more typically in the range of 50 to 250 mN/M. The SPE medium is positioned in the housing such that a liquid passing from the inlet to the outlet flows through the SPE medium. The housing is pressurizable so that the liquid can be forced through the SPE medium by exerting a positive pressure on the liquid on the upstream side of the SPE medium. The term "positive pressure" means a pressure greater than one atmosphere ($1.01325 \times 10^5$ pascals).

After the hydrophobic SPE medium has been placed in the pressurizable housing, the SPE medium is primed 12 so that an aqueous liquid can be subsequently passed therethrough. The priming of SPE medium can be accomplished by passing a water-miscible organic liquid through the SPE medium. See D. Hagen et at., 236 Membrane Approach to Solid-Phase Extractions 157–164, 159 (1990). The term "water-miscible" means the organic liquid is soluble in water; that is, at least 5 percent by volume dissolves in water at standard temperature and pressure. Preferred water-miscible organic solvents are soluble in water at all concentrations from 0 weight percent to 100 weight percent. Examples of suitable, water-miscible organic liquids include alcohols such as methanol, ethanol, and isopropanol; ketones such as acetone; acetonitrile; amides such as formamide and N,N-dimethylformamide; sulfoxides such as dimethylsulfoxide; and sulfones such as dimethyl sulfone. The priming of the hydrophobic SPE medium is carried out in a manner that allows the SPE medium to be completely immersed in the water-miscible organic liquid.

While the SPE medium is still immersed in the water-miscible organic liquid, the aqueous liquid that is to be subjected to the SPE process is fed 14 through the inlet into the housing. The aqueous liquid is continuously fed 14 under pressure into the housing to displace the water-miscible organic liquid from the SPE medium and cause the SPE medium to remain continuously immersed in aqueous liquid until the SPE process is complete. Air does not make contact with the SPE medium to render any substantial portion thereof not penetratable to fluid flow. The aqueous liquid can be any aqueous liquid capable of being processed by the SPE medium. Typical examples include river water, waste water, ground water, tap water, urine samples, etcetera.

The hydrophobic SPE medium may be any known or later developed hydrophobic SPE medium suitable for use in a pressurized system. Particularly suitable hydrophobic SPE media are Empore TM disks (3M, St. Paul, Minn.). Examples of known hydrophobic SPE media have been disclosed in the following patents: U.S. Pat. No. 5,147,539; U.S. Pat. No. 5,071,610; U.S. Pat. No. 4,971,736; U.S. Pat. No. 4,906,378; U.S. Pat. No. 4,810,381; and WO 93/00163, the disclosures of which are incorporated here by reference. The SPE media may comprise a fibrous or fibril structure, for example, a polytetrafluoroethylene fibril matrix, having sorptive, hydrophobic, particles enmeshed therein. The term "matrix" means an open-structured entangled mass of fibers. To demonstrate hydrophobicity, the particulate material can have a low surface polarity, in the range of about 0.1 to 0.5, and may be substantially insoluble in water or in the elution solvent. The particulate material can be an organic compound, a polymer, or an inorganic oxide such as silica, alumina, titania, zirconia, and other ceramics, or it can be an ion exchange resin or chelating particles. Preferred particulate material are silica and zirconia, with silica being particularly preferred because of the ease of bonding a variety of hydrophobic and semi-hydrophobic coatings onto its surface. The hydrophobic SPE medium may be in the form of a disk having a thickness of 125 to 10,000 micrometers.

Suitable particles for use in an SPE medium include any particle which can be coated with insoluble sorbent material or the surface (external and/or internal) of which can be derivatized to provide a coating of insoluble sorbent material. Preferred supports for such coatings include inorganic oxide particles, most preferably silica particles. The insoluble sorbent coatings generally have a thickness in the range of one molecular monolayer to about 300 micrometers. Such particles having coated surfaces are well known in the art, see, for example, Snyder and Kirkland, "Introduction to Modern Liquid Chromatography", 2d Ed., John Wiley & Sons, Inc. (1979) and H. Figge et at., "Journal of Chromatography" 351 (1986) 393–408. Coatings which can be applied to silica particulate can be either thin mechanical coatings of insoluble polymers such as crosslinked silicones, polybutadienes, et cetera, or covalently bonded organic groups such as aliphatic groups of varying chain length and aliphatic and aromatic groups containing amine, nitrile, hydroxyl, chiral, and other functionalities which alter the polarity of the coating.

The particulate material may have a spherical shape, a oblate or prolate shape, an irregular shape, or combinations and variations thereof. Particulate material useful in the invention has a size in the range of 0.1 to about 600 micrometers, preferably in the range of 1 to 100 micrometers.

FIGS. 2 and 3 illustrate an example of an assembly that may be used in the above-described method. Assembly 16 includes a pressurizable housing 18 that has a first-half 20 and a second-half 22. An inlet tube 24 is attached to an inlet 25 of the first-half 20 of housing 18 by a threaded fitting 26. Inlet tube 24 can communicate with a pump (not shown) which feeds a liquid to the housing under positive pressure. Inlet 25 passes through a feed portion 28 in the first-half 20 of housing 18 to direct a liquid to the interior of housing 18. A vent 30 is located in the first-half 20 of housing 18 to enable air to be released or displaced from the interior of housing 18 when the liquid layer has reached a satisfactory level in housing 18. An O-ring 31 is provided to hermetically seal the first-half 20 to the second-half 22 to provide a pressurizable housing 18. Second-half 22 of housing 18 has an outlet 32 through which the liquid passes to exit housing 18. A threaded fitting 34 is secured to an exit portion 36 in the second-half 22 of housing 18. An exit tube (not shown) may be placed in communication with outlet 32 via threaded fitting 34.

A disk support plate 38 can be employed in housing 18 to uphold a disk assembly 39 in a planar format. Disk assembly 39 includes fluid-permeable, porous sheets 42 and 44 disposed on opposite sides of SPE membrane 40. Porous sheets 42 and 44 are optional but sheet 42 may be employed as a prefilter or both sheets 42 and 44 may be used to create sufficient back pressure to cause the disk to become fully immersed in liquid. Outlet 32 may have a restrictor 46 located therein which enables a higher pressure to be achieved inside of housing 18. A cut-out portion 47 may be provided in second-half 20 of housing 18 to facilitate removal of the disk assembly 39 from housing 18.

To assure that a liquid passes through the SPE membrane 40 while that liquid is passing through housing 18, the first-half 20 can be provided with an annular flange 48 which projects towards the second-half 20 of housing 18 to retain the SPE membrane in a fixed position against support plate 38. Support plate 38 preferably has a structure such as disclosed in U.S. application Ser. No. 08/027,079 (Attorney Docket Number 49508USA1A) filed on the same day as this application by Timothy L. Hoopman and incorporated here by reference. A support plate of the construction of the Hoopman application has a plurality of concentric grooves that are intersected by a plurality of radially extending grooves. Fluid exit holes are disposed in some of the radially extending grooves at the peripheral end of the groove. This support plate assists in evenly distributing fluid flow through the SPE membrane. Improved fluid distribution can also be obtained by installing a spray head (not shown) where the inlet 25 makes full communication with the interior of housing 18 at location 50. The spray head may take the form of a threaded machine screw that has at least one slot extending through the threads of the screw. The machine screw is threaded into inlet 25 at location 50. Fluid passes from inlet 25, through the slot in the bolt to strike the screw's head and be distributed over the surface of the SPE medium. An Example of another spray head that may be suitable is disclosed in U.S. Pat. No. 4,944,876.

In operation, the SPE disk can be immersed in the liquid that is passing therethrough by venting housing 18 to the atmosphere until a liquid layer builds up over the surface of the disk. After the liquid layer is thick enough, the vent 30 to the atmosphere is closed, and additional liquid is pumped into the housing causing an increase in pressure which forces the liquid evenly through the disk 40. In lieu of a vent 30, a restrictor 46 can be employed in the outlet stream 32 to reduce liquid flow through the outlet and cause a liquid layer to build up in the housing 18. After enough liquid has built up in housing 18, the pressure will overcome the resistance to flow caused by the restrictor 46, allowing the liquid to flow through the SPE disk 441. Examples of restrictors 46 that may be suitable for use in this invention include a plate with a small opening located therein, a porous metal or plastic plate, or any other device suitable for creating resistance to fluid flow, or the size of the outlet 32 may be reduced to restrict flow. In a further embodiment neither a vent 30 nor a restrictor 46 is needed to cause the liquid to build up on the surface of the SPE disk 441, but the disk assembly 39 or SPE medium 40 itself must supply sufficient resistance to fluid flow to allow a liquid layer to build up over the SPE disk. In this embodiment, the first-half 20 of housing 18 should be provided with an interior large enough to create a compressible air column over the disk assembly 39. When the liquid layer has sufficient depth, the air in the volume above the disk assembly 39 will exert sufficient pressure on the liquid to overcome the resistance of the disk. The liquid will then flow evenly through the SPE medium.

EXAMPLES

Example 1

A housing was designed for use with Empore TM disks which were 47 millimeters (mm) in diameter and 0.5 mm thick, available from Varian Sample Preparation Products, Harbour, Calif. A housing was constructed that had an inside diameter of 48 mm. A chamber was disposed above the membrane in the housing which was 45 mm in diameter and 30 mm high. The membrane was placed on a support plate having a construction similar to the support plate shown in FIGS. 1 and 2 of the above-cited Hoopman application. The support plate was a plastic disk machined from a piece of Kel-F TM Brand polychlorotrifluoroethylene (PCTFE) thermoplastic available from 3M Company, Industrial Chemical Products. There were approximately 86 concentric, radially-spaced grooves on the upstream side of the plate. The concentric, radially-spaced grooves were about 0.28 mm deep and were spaced at about 4 grooves per millimeter. In addition to the concentric grooves, radially-extending grooves were machined into the upstream surface of the support plate in the pattern shown in Hoopman FIGS. 1 and 2. Each radially-extending groove was approximately 0.5 mm wide and 0.5 to 0.75 mm deep. A vent, constructed of a plugged tube fitting 6 mm in diameter was built into the top of the chamber. The vent could be opened (vented) and closed as needed.

The purpose of this Example was several fold: (1) to prime the membrane; (2) to have the vent open while the membrane was primed (displacing air in the chamber); and (3) to determine if a water solution containing a blue dye would pass uniformly through a primed, solid-phase extraction membrane.

The membrane was primed with 10 milliliters (ml) of methanol while the vent was left open, allowing the disk to be immersed in methanol. The vent was then closed, and the membrane was further primed with an additional 10 ml of methanol. Then 10 ml of water were pumped into the housing to displace the methanol. Then 100 ml sample of water containing a blue dye was pumped through the membrane. The dye was an Alphazurine A dye, lot CZ01712CZ, available from Aldrich Chemical Company, Inc., Milwaukee, Wis. The membrane remained completely and continuously immersed in liquid throughout the procedure. At the end of the procedure, a blast of high pressure air forced all of the liquid through the membrane. Upon visual examination, blue dye was seen to be evenly distributed over the entire surface of the membrane. No spots were observed which would indicate that air had contacted the solid-phase extraction medium. Thus, the method and apparatus of this invention demonstrated uniform flow through the membrane without permitting air to make contact with the same.

Example 2

This Example was performed in the same manner as Example 1, except the vent was left closed during the priming and extracting operations. The chamber above the membrane had sufficient volume to allow air in the chamber to be compressed to permit a layer of liquid to build up on the membrane and submerge the same.

After the extraction of the dye was complete, the Empore TM disk was visually examined. The blue dye was seen to be evenly distributed over the entire surface of the membrane. No spots were observed which would indicate that air had contacted the solid-phase extraction medium. Thus, the method and apparatus of this invention demonstrated uniform flow through the membrane without permitting air to make with the same.

Comparative Example 1

The purpose of this Example was to demonstrate that (i) the useful surface area of a hydrophobic, solid-phase extraction medium would be reduced and (ii) non-uniform flow through the solid-phase extraction medium would result, when the method and apparatus of the invention were not employed during a pressurized SPE.

This Example was performed in the same manner as Example 2, except the size of the chamber above the membrane was reduced. The chamber had the same diameter, but the height of the chamber was reduced to 1.3 mm from 30 mm. After the SPE process was completed, the SPE membrane was examined visually. There were large white spots on the membrane which covered approximately 25 to 35 percent of the membrane's surface area. The white or non-dyed areas represent the portions of the membrane through which the aqueous liquid did not penetrate the membrane. Thus, a reduction in useful surface area and a non-uniform flow was demonstrated by the pressurized system when the method and apparatus of the invention were not employed.

Example 3

The purpose of this Example was to quantitatively sorb onto an Empore TM disk a known quantity of the red dye Disperse 1 (available from Aldrich Chemical Co., Milwaukee, Wis.) in water by passing this aqueous solution through a primed membrane as described in Example 1 and then eluting the sorbed dye from the membrane and measuring the quantity of dye recovered. A one liter aqueous sample containing 100 micrograms of red dye was passed through the Empore TM disk. Three trials were performed on three separate Empore TM disks, and each disk was quantitatively eluted with methanol. The eluent was analyzed spectrophotometrically at 480 nanometers and was compared with a standard solution of the red dye. The percent recovery of the dye was for the three trials was 96.5%, 97.3%, and 99.3%, respectively, thereby demonstrating good recovery using the method and apparatus of this invention.

Example 4

The purpose of this Example was to quantitatively sorb onto the Empore TM membrane a known quantity of a plasticizer in water and measure the quantity of recovered plasticizer.

A one liter sample of a plasticizer in water (65 parts per billion) was passed through an Empore TM membrane, previously primed as described in Example 1. Each membrane was eluted with three 6 ml portions of acelonitrile. Recovery of the plasticizer was essentially quantitative as indicated in the table below.

| Plasticizer | Percent of Recovery |
| --- | --- |
| Dimethyl phthalate* | 98.0 +/− 3.0 |
| Diethyl phthalate* | 97.2 +/− 2.1 |
| Dibutyl phthalate* | 96.5 +/− 2.2 |
| Dioctyl phthalate* | 94.4 +/− 6.8 |

*These plasticizers are commercially available from Aldrich Chemical Co., Milwaukee, WI.

The data in the above table demonstrate that good analyte recoveries can be obtained using the method and apparatus of this invention.

This invention may take on various modifications and alterations without departing from the spirit and scope thereof. Accordingly, it is also to be understood that this invention is not to be limited to the above-described, but is to be controlled by the limitations set forth in the following claims and any equivalents thereof. It is also to be understood that this invention may be suitably practiced in the absence of any element not specifically disclosed herein.

What is claimed is:

1. A method of performing a solid-phase extraction on an aqueous fluid using a hydrophobic, solid-phase extraction disk, which method comprises:
   (a) placing a hydrophobic, solid-phase extraction disk inside of a pressurizable housing having an inlet and an outlet, the hydrophobic, solid-phase extraction disk being positioned in the pressurizable housing such that a liquid moving from the inlet to the outlet passes through the hydrophobic, solid-phase extraction disk;
   (b) priming the hydrophobic, solid-phase extraction disk with a water-miscible organic liquid by passing the water-miscible organic liquid from the inlet to the outlet under positive pressure; and
   (c) passing an aqueous liquid from the inlet to the outlet under positive pressure;
   wherein the water-miscible organic liquid and the aqueous liquid are passed from the inlet to the outlet such that the hydrophobic, solid-phase extraction disk is completely and continuously immersed in liquid in the pressurizable housing during steps (b) and (c).

2. The method of claim 1, wherein the pressurizable housing is vented to atmosphere to reduce the pressure inside of the housing until the hydrophobic, solid-phase extraction disk becomes immersed in step (b).

3. The method of claim 2, wherein the vent is closed after the hydrophobic, solid-phase extraction disk is completely immersed in the water-miscible organic liquid.

4. The method of claim 1, wherein the outlet in the housing has a restriction to fluid flow to enable the hydrophobic, solid-phase extraction disk to become completely and continuously immersed in liquid during steps (b) and (c).

5. The method of claim 1, wherein the hydrophobic, solid-phase extraction, disk, other fluid-permeable medium, or combinations thereof, are disposed in the housing to create sufficient back pressure to cause the hydrophobic, solid-phase extraction disk to become completely and continuously immersed in during steps (b) and (c).

6. The method of claim 1, wherein the hydrophobic, solid-phase extraction disk is a polytetrafluoroethylene fibril matrix having sorptive, hydrophobic particles enmeshed therein.

7. The method of claim 1, wherein the hydrophobic, solid-phase extraction disk contains sorptive particulate having sizes of 0.1 to 600 micrometers.

8. The method of claim 7, wherein the hydrophobic, solid-phase extraction disk has a surface energy in the range of 20 to 300 millinewtons per meter.

9. The method of claim 8, wherein the sorptive particulate has a surface polarity of 0.1 to 0.5 and a size of 1 to 100 micrometers, and the hydrophobic, solid-phase extraction disk has a surface energy of 50 to 250 millinewtons per meter.

10. The method of claim 1, wherein the hydrophobic, solid-phase extraction disk has a thickness of 125 to 10,000 micrometers.

* * * * *

UNITED STATES PATENT AND TRADEMARK OFFICE
CERTIFICATE OF CORRECTION

PATENT NO. : 5,391,298
DATED : February 21, 1995
INVENTOR(S) : Richard M. Pieper and James E. Aysta It is certified that error appears in the above-indentified patent and that said Letters Patent is hereby corrected as shown below:

Column 6, line 8, "441" should be --40--.

Signed and Sealed this

Twenty-fifth Day of April, 1995

*Attest:*

BRUCE LEHMAN

*Attesting Officer*      *Commissioner of Patents and Trademarks*

REEXAMINATION CERTIFICATE (3365th)
United States Patent [19]
Pieper et al.

[11] B1 5,391,298
[45] Certificate Issued Oct. 28, 1997

[54] METHOD FOR PERFORMING A SOLID-PHASE EXTRACTION UNDER PRESSURIZED CONDITIONS

[75] Inventors: Richard M. Pieper, St. Paul; James E. Aysta, Stillwater, both of Minn.

[73] Assignee: Minnesota Mining and Manufacturing Company, St. Paul, Minn.

Reexamination Request:
No. 90/004,130, Feb. 5, 1996

Reexamination Certificate for:
Patent No.: 5,391,298
Issued: Feb. 21, 1995
Appl. No.: 27,080
Filed: Mar. 5, 1993

Certificate of Correction issued Apr. 25, 1995.

[51] Int. Cl.$^6$ .................................................. B01D 15/00
[52] U.S. Cl. ........................... 210/638; 210/674; 210/679

[56] References Cited

U.S. PATENT DOCUMENTS

| | | | |
|---|---|---|---|
| 5,071,565 | 12/1991 | Fritz et al. | 210/692 |
| 5,198,115 | 3/1993 | Stalling et al. | 210/634 |

OTHER PUBLICATIONS

Empore™ 3M Technical Data Feb. 1991.
Toxi-News vol. 10 No. 2 Summer 1991.
Solid Phase Extraction, McDonald & Bouvier 6th Edition p. 23 Waters Milford Mass 1995.
Acti-Disk™ FMC Corporation Report 1988.
Millipore product brochure, "Microporous Membrane Filtration", p. 55.

*Primary Examiner*—Ivars C. Cintins

[57] ABSTRACT

A method of performing a solid phase extraction on an aqueous fluid using a hydrophobic, solid-phase extraction medium (40), which method comprises:

(a) placing (10) a hydrophobic, solid-phase extraction medium (40) inside of a pressurizable housing (18) having an inlet (25) and an outlet (32), the hydrophobic, solid-phase extraction medium (40) being positioned in the pressurizable housing (18) such that a liquid moving from the inlet (25) to the outlet (32) passes through the solid-phase extraction medium (40);

(b) priming (12) the hydrophobic, solid-phase extraction medium (40) with a water-miscible organic liquid by passing the water-miscible organic liquid from the inlet (25) to the outlet (32) under positive pressure; and (c) passing (14) an aqueous liquid from the inlet (25) to the outlet (32) under positive pressure;

wherein the water-miscible organic liquid and aqueous liquid are passed from the inlet (25) to the outlet (32) such that the solid-phase extraction medium (40) is completely and continuously immersed in liquid in the pressurizable housing (18) during steps (b) and (c).

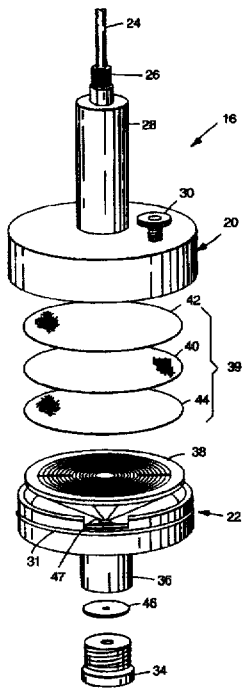

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–10 are cancelled.

* * * * *